United States Patent [19]

Fitoussi et al.

[11] 4,349,350

[45] Sep. 14, 1982

[54] PROCESS FOR THE DETERMINATION OF URANIUM (VI) OR DIALKYL DITHIOPHOSPHORIC ACID PRESENT IN AN ORGANIC SOLVENT

[75] Inventors: Richard Fitoussi, Paris; Sylvie Lours, Chatenay Malabry; Claude Musikas, Villebon, all of France

[73] Assignee: Commissariat a l'Energie Atomique, Paris, France

[21] Appl. No.: 242,655

[22] Filed: Mar. 11, 1981

[30] Foreign Application Priority Data

Mar. 17, 1980 [FR] France .................. 80 05908

[51] Int. Cl.³ ............................. G01N 21/00
[52] U.S. Cl. .................. 23/230 R; 23/230 M
[58] Field of Search ................ 23/230 R, 230 M

[56] References Cited

U.S. PATENT DOCUMENTS

| | | | |
|---|---|---|---|
| 2,976,122 | 3/1961 | Ertelt et al. | 23/230 R |
| 3,099,537 | 7/1963 | Mason et al. | 23/230 R |
| 3,104,941 | 9/1963 | Hart et al. | 23/230 X |
| 3,403,004 | 9/1968 | Jungreis et al. | 23/230 R |
| 3,976,428 | 8/1976 | Link | 23/230 R |

*Primary Examiner*—Ronald E. Serwin
*Attorney, Agent, or Firm*—Pearne, Gordon, Sessions, McCoy & Granger

[57] ABSTRACT

The invention relates to a process for the determination of uranium (VI) or dialkyl dithiophosphoric acid present in an organic solvent.

In this process, a dialkyl dithiophosphoric acid or a uranium (VI) salt is added to the organic solvent so as to convert all the uranium or dialkyl dithiophosphoric acid present in said solvent into a mixed uranium (VI) - dialkyl dithiophosphoric acid-organophosphorus compound complex. The optical density of the solvent containing the complex in solution is measured so as to determine the concentration of this solvent in the complex, together with its uranium dialkyl dithiophosphoric acid content.

Application to the determination of traces of uranium in tributylphosphate obtained from the reprocessing of irradiated fuels.

13 Claims, 4 Drawing Figures

PROCESS FOR THE DETERMINATION OF URANIUM (VI) OR DIALKYL DITHIOPHOSPHORIC ACID PRESENT IN AN ORGANIC SOLVENT

BACKGROUND OF THE INVENTION

The present invention relates to a process for the determination of uranium (VI) or dialkyl dithiophosphoric acid present in an organic solvent comprising a neutral organophosphorus compound with an electron donor oxygen atom, such as an organic solvent constituted by tributylphosphate diluted in dodecane.

It is known that in installations for extracting uranium ores or in installations for the reprocessing of irradiated fuels, uranium extraction generally takes place in an organic solvent, followed by the reextraction of this uranium in an aqueous solution.

In order to be able to check the operation of such installations, it is important to be able to rapidly establish the residual uranium contents of the organic solvents leaving the reextraction stage.

At present, the uranium present in such organic solvents is determined by a colorimetric method using dibenzoyl methane. However, this method requires complex operations, so that it is not possible to easily and rapidly obtain the results of the determination. Moreover, with this method the colouring is due to an intramolecular transition of the attached ligand, which is not specific.

BRIEF SUMMARY OF THE INVENTION

The present invention relates to a process for the determination of the uranium or dialkyl dithiophosphoric acid present in an organic solvent, which has the advantage of being simple, fast and reliable.

The present invention therefore relates to a process for the determination of the uranium (VI) or dialkyl dithiophosphoric acid present in an organic solvent comprising a neutral organophosphorus compound with an electron donor oxygen atom, wherein a dialkyl dithiophosphoric acid or a uranium (VI) salt is added to the organic solvent so as to convert all the uranium (VI) or dialkyl dithiophosphoric acid present in the solvent into a mixed uranium (VI)-dialkyl dithiophosphoric acid-organophosphorus compound complex and wherein the optical density of the solvent containing this complex in solution is measured so as to determine the concentration of the complex in the solvent, as well as its uranium or dialkyl dithiophosphoric acid content.

According to the process of the invention, the uranium (VI) or dialkyl dithiophosphoric acid is converted into a uranium (VI)-organophosphorus compound-dialkyl dithiophosphoric acid complex either by reacting the uranium with a dialkyl dithiophosphoric acid excess, or by reacting the dialkyl dithiophosphoric acid with an excess of uranium (VI) ions.

The formation of this complex corresponds to the following reaction diagram:

$$UO_2^{2+} + A_2S_2 + 2HDTP \rightleftharpoons [UO_2(DTP)_2S] + 2HA + S$$

in which S represents a neutral organophosphorus compound with an electron donor oxygen atom, HDTP stands for a dialkyl dithiophosphoric acid and A stands for an anion such as $Cl^-$ or $NO_3^-$.

In view of the fact that the thus obtained complex which has a relatively intense sulphur-uranium charge transfer band is coloured, its concentration in the solvent can then be measured by spectrophotometry, which makes it possible to determine the concentration of uranium (VI) or dialkyl dithiophosphoric acid in the organic solvent.

This determination process has the advantage of being very simple to perform and of being very easily automated. Thus, it is merely necessary to add a single reagent constituted either as a uranium salt or dialkyl dithiophosphoric acid to the organic solvent with no change of phase and then measure the optical density of the solvent.

Moreover, it makes it possible to determine traces of uranium with a good level of accuracy, particularly in the uranium concentration range of $2 \cdot 10^{-5}$ to $5 \cdot 10^{-4}$ M/l.

According to the invention, the organophosphorus compound comprising an electron donor oxygen atom present in the organic solvent is advantageously tributylphosphate or a compound in accordance with the following formula:

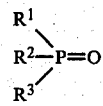

in which $R^1$, $R^2$ and $R^3$, which can be the same or different, represent an alkyl, alkoxyalkyl or aryl radical.

Examples of such organophosphorus compounds are trioctylphosphine oxide, di-n-hexyloctoxymethyl phosphine oxide, di-phenyl-octoxymethyl phosphine oxide, di-isobutyl-octoxymethyl phosphine oxide, di-n-butyl-octoxymethyl phosphine oxide and di-n-pentyl-octoxymethyl phosphine oxide.

According to a first embodiment of the process of the invention intended for the determination of the uranium (VI) present in an organic solvent a dialkyl dithiophosphoric acid excess is added to the organic solvent in such a way that all the uranium present in the organic solvent is converted into a mixed uranium-dialkyl dithiophosphoric acid-organophosphorus compound complex and the optical density of the solvent containing the complex is measured so as to determine the concentration of the organic solvent in the complex and its uranium content.

According to the invention, the dialkyl dithiophosphoric acid is advantageously constituted by di-2-ethyl-hexyl-dithiophosphoric acid, dibutyl dithiophosphoric acid or bis(2,6-dimethyl-4-heptyl)dithiophosphoric acid. Preference is given to the use of dibutyl dithiophosphoric acid.

According to the invention, for complexing all the uranium present in the organic solvent, a quantity of dialkyl dithiophosphoric acid is added to the solvent such that it corresponds to an acid excess compared with the uranium quantity present in the organic solvent.

Moreover, when the process of the invention is used for determining the uranium in a solvent used for the extraction of uranyl nitrate a larger dialkyl dithiophosphoric acid excess is used, because part of this reagent can be degraded by nitrous ions which may be present in the organic solvent containing the uranyl nitrate.

It is advantageous to use a dialkyl dithiophosphoric acid concentration exceeding 0.1 M/l of solvent for uranium concentrations of 5 to 100 mg/l.

After forming the complex, the optical density of the organic solvent containing the complex is measured by means of conventional equipment such as a spectrophotometer, advantageously at a wavelength of 390 nm.

According to a second embodiment of a process of the invention for determining the dialkyl dithiophosphoric acid present in an organic solvent an excess of uranium (VI) salt is added to the organic solvent so as to convert all the dialkyl dithiophosphoric acid present in the solvent into a mixed uranium-dialkyl dithiophosphoric acid-organophosphorus compound complex and the optical density of the solvent containing the complex is measured so as to determine the concentration of the solvent in the complex and its dialkyl dithiophosphoric acid content.

The uranium salt used can be uranyl chloride or nitrate. Preferably, uranyl chloride is used, because it does not lead to the formation of disturbing by-products.

This second embodiment of the process of the invention can be used for determining traces of a dialkyl dithiophosphoric acid, such as dibutyl dithiophosphoric acid, di-2-ethylhexyl-dithiophosphoric acid and bis(2,6-dimethyl-4-heptyl)dithiophosphoric acid.

BRIEF DESCRIPTION OF THE DRAWINGS

The invention is described in greater detail hereinafter relative to non-limitative embodiments and with reference to the attached drawings, wherein show.

DETAILED DESCRIPTION OF THE PREFERRED EMBODIMENTS

EXAMPLE 1

This example relates to the determination of uranium traces present in an organic solvent constituted by tributylphosphate diluted in dodecane (hyfrane), the tributylphosphate content of the solvent being 30% by volume, which corresponds to industrially used solvents.

A quantity of dibutyl dithiophosphoric acid is added to the solvent containing the uranium traces in such a way that it corresponds to 0.2 M of acid per liter of solvent. The optical density of the thus treated solvent is then determined at a wavelength of 390 nm using a CARY 17 spectrophotometer.

Figure 1:
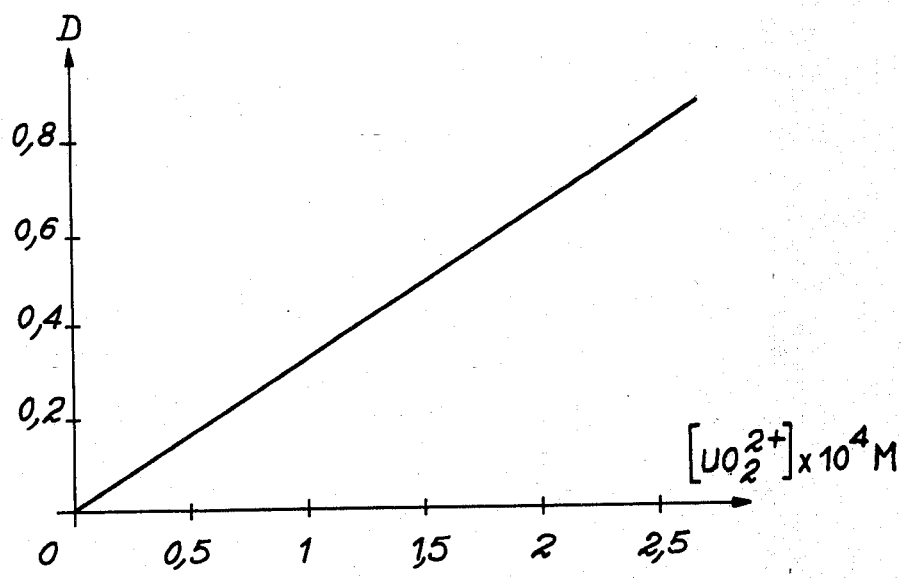
FIG. 1 a graph showing the variations in the optical density of the solvent at 390 nm, as a function of its uranium concentration.

The results obtained with solutions, whose uranium concentration varies from 0 to $2.5 \cdot 10^{-1}$ M/l are given in FIG. 1, which shows the variations of the optical density D of the solvent, as a function of the uranium concentration of the initial solution determined by potassium dichromate potentiometry.

On the basis of this graph, it is possible to see that the Beer-Lambert law has been verified, because the optical density D of the solvent increases in a linear manner with its uranium content, i.e. with its complex content, which corresponds to the equation:

$$D = \epsilon l C$$

in which $\epsilon$ represents the molar extinction coefficient, $l$ the length of the spectrophotometer vessel and C the concentration in complex of the solvent.

It was also found that the results obtained were similar when the optical density measurement was performed at 360 nm, with the exception of the molar extinction coefficient which was then higher.

Finally, by using different dibutyl dithiophosphoric acid concentrations, the same results were obtained and it was found that the molar extinction coefficients at 390 nm are approximately 3260, as is shown by the results of the following table.

TABLE

| DBDTP(M) acid concentration | $\epsilon$ |
|---|---|
| 0.05 | 3260 |
| 0.1 | 3280 |
| 0.15 | 3240 |

EXAMPLE 2

This example relates to the determination of dibutyl dithiophosphoric acid traces in an organic solvent constituted by tributylphosphate diluted in dodecane (30% tributylphosphate, 70% hyfrane).

A uranium salt constituted either by uranyl nitrate, or uranyl chloride is added to the organic solvent containing the dibutyl dithiophosphoric acid traces in a quantity such that it corresponds to a uranium salt concentration in the organic solvent of $3 \cdot 10^{-2}$ M/l of solvent. The optical density of the solvent is then measured by using a spectrocolorimeter at 390 nm.

Figure 2:
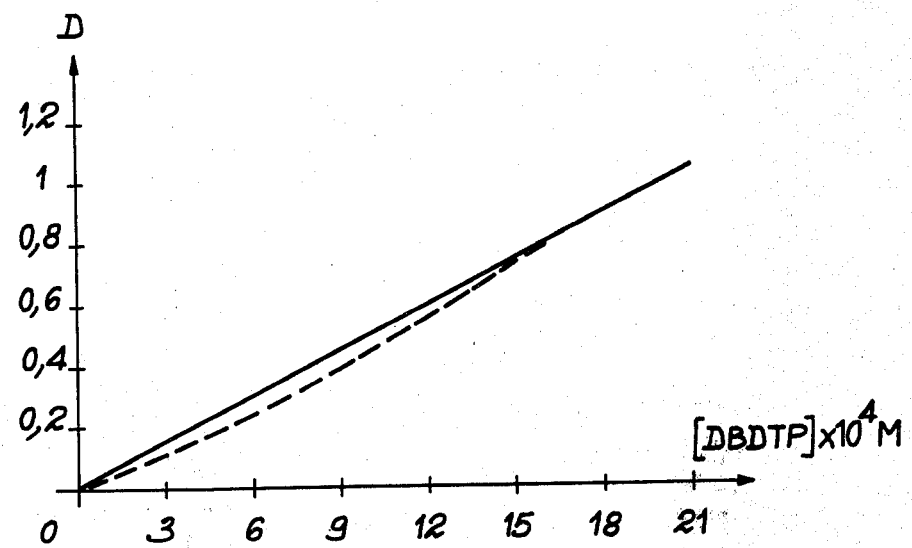
FIG. 2 a graph showing the variations of the optical density of the solvent at 390 nm as a function of its dibutyl dithiophosphoric acid (DBDTP) concentration.

The results obtained for various dibutyl dithiophosphoric acid concentrations in the solvent are given in FIG. 2, which shows the optical density variations of the solvent as a function of its dibutyl dithiophosphoric acid concentration.

In FIG. 2, the straight line corresponds to the determination carried out by means of uranyl chloride and the dotted line curve to the determination carried out by using uranyl nitrate.

Thus, when using uranyl nitrate, the Beer-Lambert law is not respected for further low dibutyl dithiophosphoric acid concentrations. In this case, it is assumed that the uranyl nitrate which is obtained by the extraction of uranium in a nitric medium contains a certain quantity of nitrous acid which degrades the dibutyl dithiophosphoric acid in accordance with the following reaction diagram.

$$2(C_4H_9O)_2P\begin{matrix}\diagup S \\ \diagdown SH\end{matrix} + 2NO_2H \longrightarrow$$

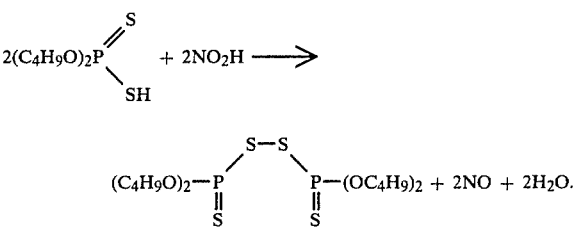

Thus, for the measurement of small dibutyl dithiophosphoric acid concentrations, it is preferable to add uranium in the form of chloride, rather than in the form of nitrate.

However, satisfactory results can be obtained with uranyl nitrate by following the optical density of the solvent as a function of time, in order to determine by extrapolation the concentration of the solvent in the complex at the time of mixing and as illustrated in the following example 3.

EXAMPLE 3

In this example, the stability of the colouring of the solvent is studied as a function of time in the case of the determination of small dibutyl dithiophosphoric acid quantities by means of uranyl chloride or uranyl nitrate.

In order to carry out this determination, to an organic solvent identical to that of examples 1 and 2 with a dibutyl dithiophosphoric acid concentration of $10^{-3}$ M is added an excess of uranyl nitrate or uranyl chloride. The optical density of the organic solvent treated in this way at 390 nm is then measured using the same spectrocolorimeter as in example 2 and its evolution as a function of time is followed.

Figure 3:
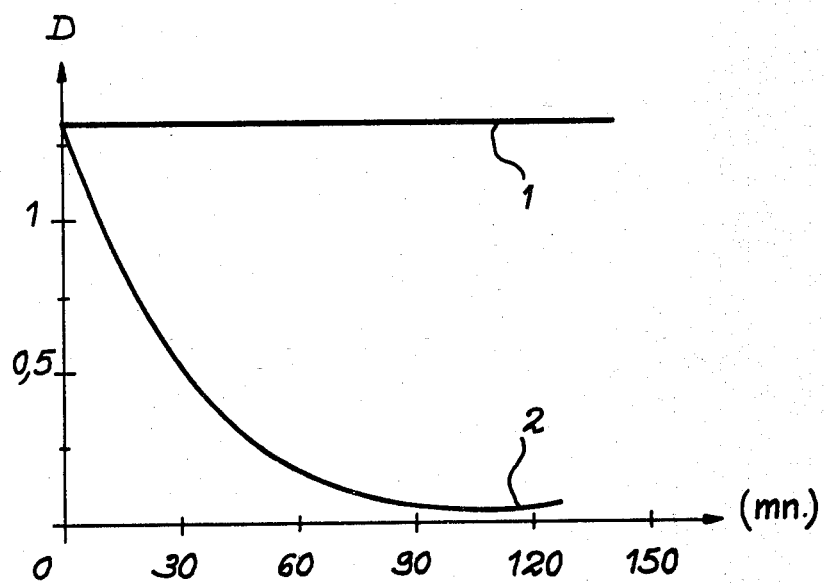
FIG. 3 a graph showing the variations of the optical density of the solvent at 390 nm as a function of time (in minutes) in the case where there are chloride ions (curve 1) or nitrate ions (curve 2) in the organic solution, the dibutyl dithiophosphoric acid concentration being close to 0.001 M in both cases.

The results obtained are given in FIG. 3 which illustrates the variations of the optical density D as a function of time in minutes, curve 1 relating to the case of adding uranyl chloride and curve 2 to the case of adding uranyl nitrate.

In the case of curve 2, the colouring rapidly disappears, which confirms the hypothesis of a degradation of the reagent by an oxidizing agent, such as the nitrous acid present in the solvent.

EXAMPLE 4

This example illustrates the influence of the presence of dibutyl phosphoric acid traces in the organic solvent and the results obtained by the process of the invention.

It is known that during the reprocessing of irradiated fuels, the organic solvents constituted by tributylphosphate are degraded by hydrolysis and alpha radiolysis, whilst in particular giving dibutyl phosphoric acid as a by-product. Furthermore, the presence of this by-product is detrimental when carrying out a colorimetric determination of the uranium by complex formation, because it is a good uranium complexing agent.

This example studies the influence of the dibutyl phosphoric acid concentration of the organic solvent on the results obtained by the determination process according to the invention.

The organic solvents used are the same as for example 1, each containing $3 \cdot 10^{-4}$ M/l of $UO_2^{2+}$ and variable dibutyl phosphoric acid quantities.

For carrying out the determination, 0.2 M/l of dibutyl dithiophosphoric acid is added to the solvent. The optical density of the thus treated solvent is then determined at 390 nm, using the same spectrocolorimeter as in example 2.

Figure 4:
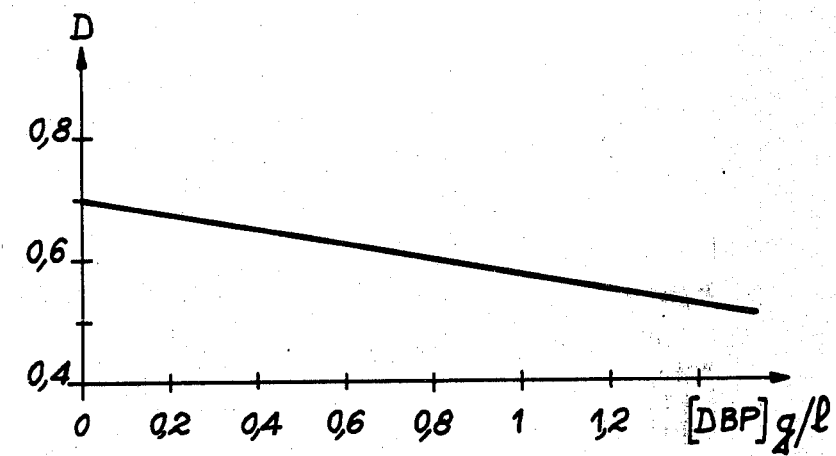
FIG. 4 a graph showing the variations of the optical density of the solvent at 390 nm as a function of its dibutyl phosphoric acid content.

The results are given in FIG. 4, which shows the variations of the optical density as a function of the dibutyl phosphoric acid (DBP) concentration of the solvent (in g/l).

It can be gathered from FIG. 4 that the optical density is only slightly modified when the dibutyl phosphoric acid concentration is below 0.2 g/l, which is generally the case in organic solvents produced by irradiated fuel processing installations. In addition, the presence of dibutyl phosphoric acid does not appear to particularly impair the colorimetric determination.

Moreover, to obviate any possible influence thereof on the results of the determination, it is possible to use the internal calibration method consisting of carrying out two optical density measurements, one on the solvent to be determined and on the other to the solvent to be determined to which is added a standard solvent, in order to obtain the unknown concentration by extrapolation.

What is claimed is:

1. A process for the determination of the uranium (VI) or dialkyl dithiophosphoric acid present in an organic solvent comprising a neutral organophosphorus compound with an electron donor oxygen atom, wherein a dialkyl dithiophosphoric acid or a uranium (VI) salt is added to the organic solvent so as to convert all the uranium (VI) or dialkyl dithiophosphoric acid present in the solvent into a mixed uranium (VI)-dialkyl dithiophosphoric acid-organophosphorus compound complex and wherein the optical density of the solvent containing this complex in solution is measured so as to determine the concentration of the complex in the solvent, as well as its uranium or dialkyl dithiophosphoric acid content.

2. A process according to claim 1, wherein the neutral organophosphorus compound with an electron donor oxygen atom is in accordance with the following formula:

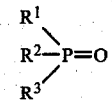

wherein $R^1$, $R^2$ and $R^3$, which can be the same or different, represent an alkyl, alkoxyalkyl or aryl radical.

3. A process according to claim 2, wherein the neutral organophosphorus compound is selected from the group containing trioctyl phosphine oxide and di-n-hexyloctoxymethyl phosphine oxide.

4. A process according to claim 1, wherein the neutral organophosphorus compound with an electron donor oxygen atom is tributylphosphate.

5. A process for uranium (VI) determination according to claim 1, wherein a dialkyl dithiophosphoric acid excess is added to the organic solvent in such a way that all the uranium present in the organic solvent is converted into a mixed uranium-dialkyl dithiophosphoric acid-organophosphorus compound complex and the optical density of the solvent containing the complex is measured so as to determine the concentration of the organic solvent in the complex and its uranium content.

6. A process according to claim 5, wherein the dialkyl dithiophosphoric acid is dibutyl dithiophosphoric acid.

7. A process according to claims 5 or 6, wherein the optical density of the solvent is measured at 390 nm.

8. A process according to claim 5, wherein the quantity of dialkyl dithiophosphoric acid added to the solvent exceeds 0.1 M of acid per liter of solvent.

9. A process according to claim 1 for the determination of dialkyl dithiophosphoric acid, wherein an excess of uranium (VI) salt is added to the organic solvent so as to convert all the dialkyl dithiophosphoric acid present in the solvent into a mixed uranium-dialkyl dithiophosphoric acid-organophosphorus compound complex and the optical density of the solvent containing the complex is measured so as to determine the concentration of the solvent in the complex and its dialkyl dithiophosphoric acid content.

10. A process according to claim 9, wherein the uranium salt is uranyl nitrate.

11. A process according to claim 9, wherein the uranium salt is uranyl chloride.

12. A process according to claim 9, wherein the optical density is measured at 390 nm.

13. A process according to claim 9, wherein the dialkyl dithiophosphoric acid is di-2-ethylhexyl-dithiophosphoric acid, dibutyl dithiophosphoric acid or bis(2,6-dimethyl-4-heptyl)dithiophosphoric acid.

* * * * *